United States Patent
Wang

(10) Patent No.: US 9,271,649 B2
(45) Date of Patent: Mar. 1, 2016

(54) IMAGING APPARATUS INCLUDING A LENS ROTATABLY CONNECTED TO A FRONT COVER

(71) Applicant: ALTEK BIOTECHNOLOGY CORPORATION, Taipei (TW)

(72) Inventor: Peng-Hsiang Wang, Hsinchu (TW)

(73) Assignee: ALTEK BIOTECHNOLOGY CORPORATION, Taipei (TW)

( * ) Notice: Subject to any disclaimer, the term of this patent is extended or adjusted under 35 U.S.C. 154(b) by 66 days.

(21) Appl. No.: 13/783,408

(22) Filed: Mar. 4, 2013

(65) Prior Publication Data

US 2014/0192322 A1 Jul. 10, 2014

(30) Foreign Application Priority Data

Jan. 8, 2013 (TW) .............................. 102100602 A

(51) Int. Cl.
*A61B 3/00* (2006.01)
*A61B 3/14* (2006.01)
*A61B 3/12* (2006.01)
*A61B 3/15* (2006.01)
*A61B 3/125* (2006.01)
*A61B 3/117* (2006.01)

(52) U.S. Cl.
CPC . *A61B 3/12* (2013.01); *A61B 3/154* (2013.01); *A61B 3/117* (2013.01); *A61B 3/125* (2013.01)

(58) Field of Classification Search
CPC ...... A61B 3/117; A61B 3/125; A61B 3/1173; A61B 3/1176
USPC .......... 351/200, 205–206, 216, 219, 221, 245
See application file for complete search history.

(56) References Cited

U.S. PATENT DOCUMENTS

| | | | | |
|---|---|---|---|---|
| 3,390,931 A * | 7/1968 | Luning | ................. | G02B 23/16 356/213 |
| 4,964,717 A * | 10/1990 | Koester | ................. | A61B 3/125 351/205 |
| 5,255,025 A * | 10/1993 | Volk | ................. | A61B 3/125 351/205 |
| 5,526,074 A * | 6/1996 | Volk | ................. | A61B 3/125 351/205 |
| 5,841,510 A * | 11/1998 | Roggy | ................. | A61B 3/125 351/218 |
| 6,183,085 B1 * | 2/2001 | Roggy | ................. | A61B 3/117 351/200 |
| 6,830,347 B2 * | 12/2004 | Slawson | ................. | A61B 3/125 351/219 |
| 7,360,896 B2 | 4/2008 | Liang et al. | | |
| 7,488,074 B2 * | 2/2009 | Siminou | ................. | A61B 3/0083 351/245 |
| 7,666,190 B2 * | 2/2010 | Tano | ................. | A61F 2/1662 600/236 |
| 7,802,884 B2 * | 9/2010 | Feldon | ................. | A61B 3/1208 351/206 |
| 8,033,665 B2 | 10/2011 | Ferguson et al. | | |
| 8,469,952 B2 * | 6/2013 | Muller | ................. | A61B 18/14 606/41 |
| 2006/0146284 A1 * | 7/2006 | Collins | ................. | A61B 3/1208 351/215 |
| 2010/0118269 A1 * | 5/2010 | Shea | ................. | A61B 3/13 351/219 |
| 2010/0265460 A1 * | 10/2010 | Mann | ................. | A61B 3/13 351/214 |
| 2012/0257167 A1 * | 10/2012 | Gille | ................. | A61B 3/117 351/219 |
| 2013/0103014 A1 * | 4/2013 | Gooding | ................. | A61B 3/102 606/6 |

(Continued)

*Primary Examiner* — Thomas K Pham
*Assistant Examiner* — Nicholas R Pasko
(74) *Attorney, Agent, or Firm* — Jianq Chyun IP Office

(57) ABSTRACT

An imaging apparatus configured to capture an image of an object to be detected is provided. The imaging apparatus includes an imaging unit, a lens, and a front cover. The lens is located on the imaging unit and has a first optical axis. The front cover is rotatably connected to the lens. Relative locations of the front cover and the object are fixed by the leaning-against of the front cover. The lens is rotated with respect to the front cover, so that the first optical axis is rotated with respect to the object.

7 Claims, 6 Drawing Sheets

(56) References Cited

U.S. PATENT DOCUMENTS

2013/0103145 A1* 4/2013 John ............... A61F 2/1662 623/6.12

2013/0182223 A1* 7/2013 Wardle ............... A61B 3/117 351/219

* cited by examiner

IMAGING APPARATUS INCLUDING A LENS ROTATABLY CONNECTED TO A FRONT COVER

CROSS-REFERENCE TO RELATED APPLICATION

This application claims the priority benefit of Taiwan application serial no. 102100602, filed on Jan. 8, 2013. The entirety of the above-mentioned patent application is hereby incorporated by reference herein and made a part of this specification.

BACKGROUND OF THE INVENTION

1. Field of the Invention

The invention relates to an optical apparatus. More particularly, the invention relates to an imaging apparatus.

2. Description of Related Art

Eyes are the window to the soul. Since people nowadays often show signs of strained vision, and more and more people suffer from ophthalmic diseases (e.g., incidence of myopia), eye care on a daily basis has become a necessity for all. Important organs in the eyes, such as retinas and macula lutea, are mostly located at the rear of the eyes (i.e., the fundus), and therefore ocular fundus examination plays a decisive role in eye care. Generally, the ocular fundus examination and diagnosis are performed by shooting images of the fundus of a patient with use of a large-sized ophthalmoscope. The large-sized ophthalmoscope is bulky and requires professional operation for taking clear fundus images. Due to a pupil size limit of human eye, when the image of the fundus is taken, paramedics are often required to adjust the ophthalmoscope to focus on different parts of the fundus. Therefore, such an ophthalmoscope is equipped with at least two moving mechanisms and relevant driving devices, which leads to the high cost barrier and the bulkiness of the ophthalmoscope. Since the paramedics and patients are burdened with the significant time consumed on taking the images of the fundus, and the costs of the ophthalmoscope employed in the hospitals and clinics are considerable, it is rather difficult to popularize the ocular fundus examination.

SUMMARY OF THE INVENTION

The invention is directed to an imaging apparatus that is able to capture images of a to-be-detected object in different directions.

In an embodiment of the invention, an imaging apparatus configured to capture an image of an object to be detected is provided. The imaging apparatus includes an imaging unit, a lens, and a front cover. The lens is located on the imaging unit and has a first optical axis. The front cover is rotatably connected to the lens, and relative positions of the front cover and the object are fixed by leaning-against of the front cover. The lens is rotated with respect to the front cover, such that the first optical axis is rotated with respect to the object.

According to an embodiment of the invention, the object is an eyeball which has a second optical axis. When the lens is rotated with respect to the front cover, the first optical axis is rotated with respect to the second optical axis.

According to an embodiment of the invention, the front cover is rotatably connected to the lens through a universal joint.

According to an embodiment of the invention, the universal joint has a first element and a second element, one of the first element and the second element is connected to the lens, and the other is connected to the front cover. The first element has a first positioning portion, and the second element has a plurality of second positioning portions. When the lens is rotated with respect to the front cover, the first positioning portion is selectively jointed to one of the second positioning portions. When the first positioning portion is jointed to the different second positioning portions, the lens is respectively in different orientations with respect to the front cover.

According to an embodiment of the invention, the imaging unit includes an image sensor and a control unit. The image sensor is located on a transmission path of light from the lens to capture an image generated by the light which comes from the lens. The control unit is electrically connected to the image sensor. Here, the control unit combines a plurality of images which are sensed by the image sensor and located at a plurality of different angles, and the images at the different angles are captured by the image sensor when the first positioning portion is jointed to the different second positioning portions.

According to an embodiment of the invention, the imaging apparatus further includes a plurality of switch elements electrically connected to the control unit. When the first positioning portion is jointed to the different second positioning portions, the switch elements are respectively triggered.

According to an embodiment of the invention, the switch elements are located between the lens and the front cover.

According to an embodiment of the invention, the imaging apparatus further includes a user's interface electrically connected to the control unit. When one of the switch elements is triggered, the user's interface informs a user that the imaging apparatus is located at an image capturing angle corresponding to the triggered switch element.

According to an embodiment of the invention, the user's interface is a display unit. When the switch elements are respectively triggered, the display unit respectively shows different patterns. Locations of the patterns on the display unit respectively correspond to the orientations of the lens with respect to the front cover.

According to an embodiment of the invention, the control unit selectively instructs the display unit to flash one of the patterns, so as to remind the user of rotating the lens with respect to the front cover to an orientation corresponding to the flashed one of the patterns. When the lens is rotated with respect to the front cover to the orientation corresponding to the flashed one of the patterns, the control unit instructs the display unit to continuously show the one of the patterns.

According to an embodiment of the invention, the front cover includes a lens ring close to a junction of the front cover and the lens, and a user holds the lens ring to rotate the front cover with respect to the lens.

According to an embodiment of the invention, the object is an eyeball, and the front cover leans against tissues around the eyeball.

As discussed above, in the imaging apparatus provided in an embodiment of the invention, the lens may be rotated with respect to the front cover, and thus the imaging apparatus is capable of detecting images of a to-be-detected object in various directions.

In order to make the aforementioned and other features and advantages of the invention more comprehensible, embodiments accompanying figures are described in detail below.

BRIEF DESCRIPTION OF THE DRAWINGS

The accompanying drawings are included to provide further understanding, and are incorporated in and constitute a part of this specification. The drawings illustrate exemplary embodiments and, together with the description, serve to explain the principles of the invention.

DETAILED DESCRIPTION OF DISCLOSED EMBODIMENTS

Figure 1A:
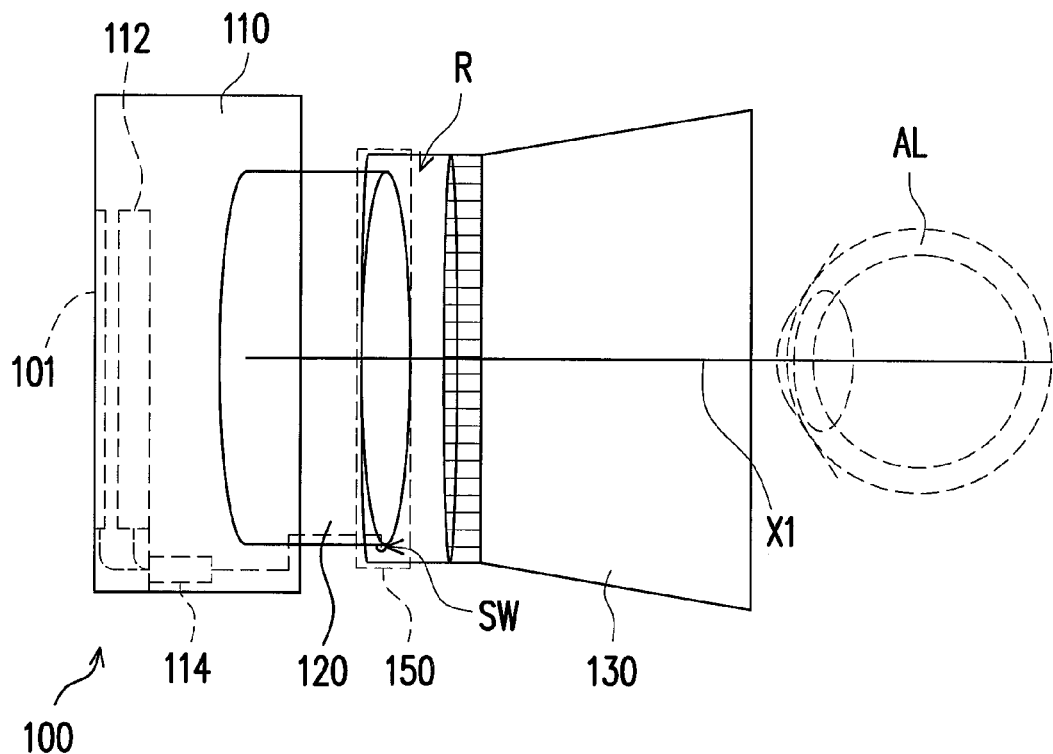
FIG. 1A, FIG. 1B, and FIG. 1C are schematic views respectively illustrating an imaging apparatus in three different operational states according to an embodiment of the invention.
Figure 1B:
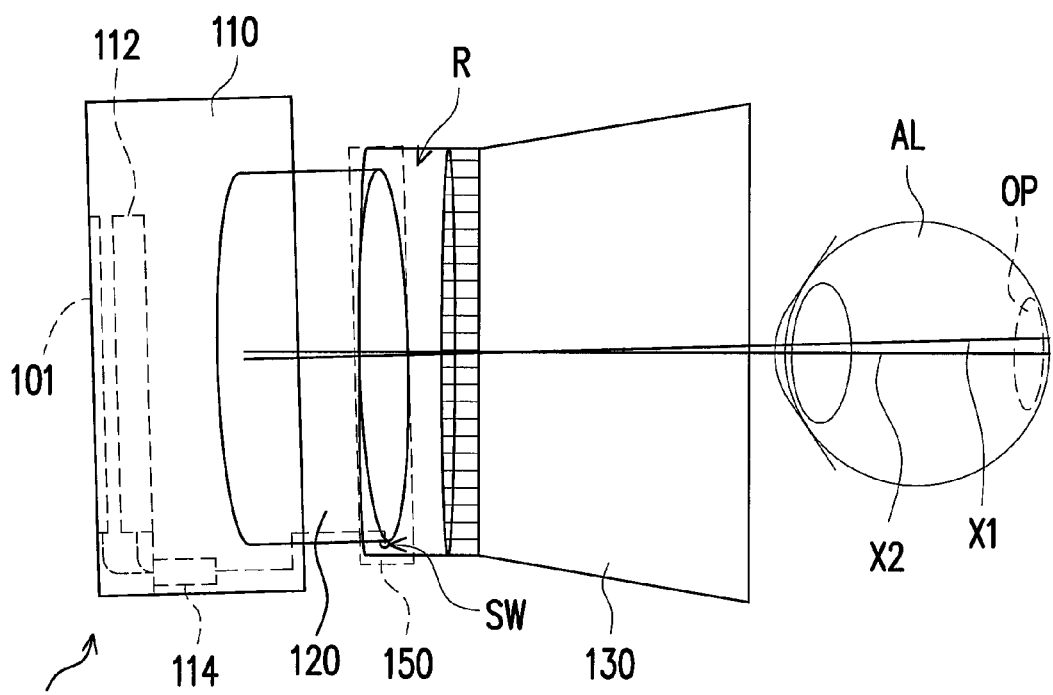
Figure 1C:
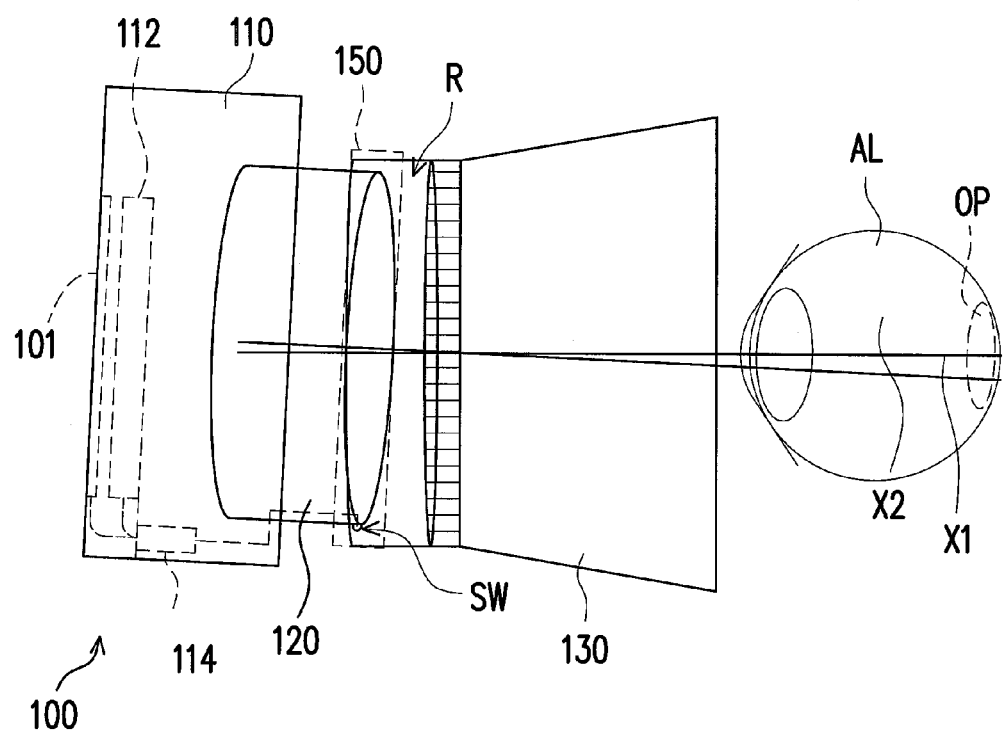

FIG. 1A, FIG. 1B, and FIG. 1C are schematic views respectively illustrating an imaging apparatus in three different operational states according to an embodiment of the invention. With reference to FIG. 1A, FIG. 1B, and FIG. 1C, an imaging apparatus 100 described in the present embodiment is suitable for capturing an image of an object AL to be detected. In the present embodiment, the imaging apparatus 100 includes an imaging unit 110, a lens 120, and a front cover 130. The lens 120 is located on the imaging unit 110 and has a first optical axis X1. The front cover 130 is rotatably connected to the lens 120, and relative positions of the front cover 130 and the object AL are fixed by the leaning-against of the front cover 130. For instance, the object AL is an eyeball, and the front cover 130 may lean against tissues around the eyeball, so as to fix the relative positions of the front cover 130 and the eyeball. The lens 120 is rotated with respect to the front cover 130, such that the first optical axis X1 is rotated with respect to the object AL.

According to the present embodiment, the object AL is an eyeball which has a second optical axis X2. The first optical axis X1 may be inclined relative to the second optical axis X2 or may be parallel to the second optical axis X2. When the lens 120 is rotated with respect to the front cover 130, the first optical axis X1 is rotated with respect to the second optical axis X2. For instance, the lens 120 may be parallel to the front cover 130, as shown in FIG. 1A, and the imaging unit 110 may focus on the center of the eyeball and shoot the image of the eyeball. Alternatively, the lens 120 may be inclined relative to the front cover 130 and rotated to the status as shown in FIG. 1B, so as to shoot images, or the lens 120 may be inclined relative to the front cover 130 and rotated to another status as shown in FIG. 1C, so as to shoot images. That is, the first optical axis X1 of the lens 120 in the imaging apparatus 100 may be aligned with different parts of the fundus OP of the eyeball so as to shoot a plurality of images. In addition, according to the present embodiment, the front cover 130 is made of a light-shielding material that may block light; thus, the front cover 130 may block the ambient stray light and further improve reliability and accuracy of shooting the images of the fundus for the purpose of clinical diagnosis of ophthalmic diseases. When the front cover 130 is made of a disposable material, ocular infection which may be caused by plural patients can be precluded, thus satisfying the sanitary requirement and preventing epidemics. The front cover 130 may further include a lens ring R close to a junction of the front cover 130 and the lens 120, and a user may hold the lens ring R and the imaging unit 110 respectively with two hands, such that the lens 120 may be rotated with respect to the front cover 130. In the present embodiment, the outer edge of the lens ring R may have bar-shape patterns with an uneven contour. When the user holds the lens ring R to rotate the lens 120, the bar-shape patterns with an uneven contour may increase friction between the hand of the user and the lens ring R; thereby, the user may hold and rotate the lens 120 stably, the use of the imaging apparatus 100 is rather convenient, and the image-shooting reliability may be improved.

Figure 2A:
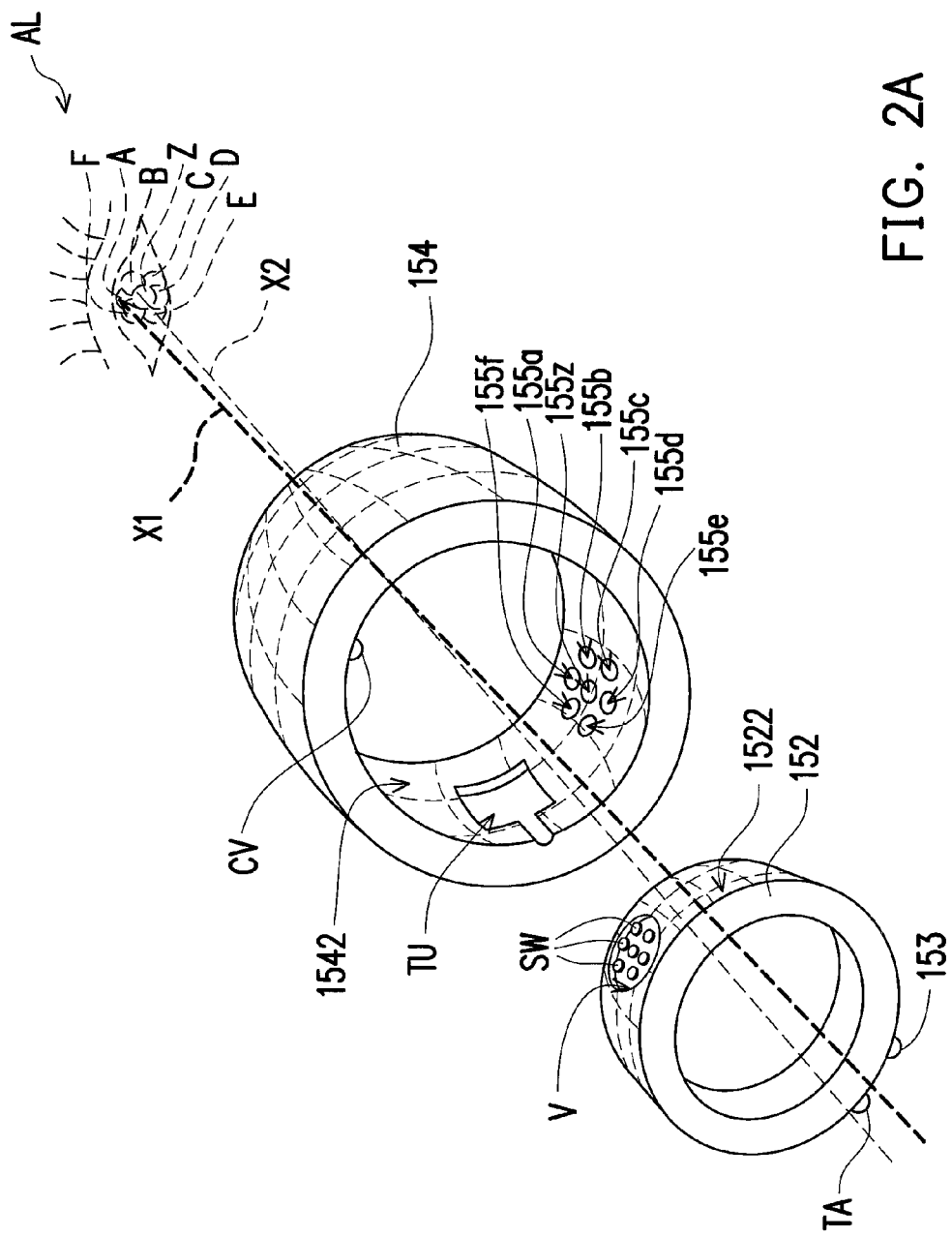
FIG. 2A and FIG. 2B are schematic partial exploded views illustrating the front cover and the lens depicted in FIG. 1A at two different viewing angles.
Figure 2B:
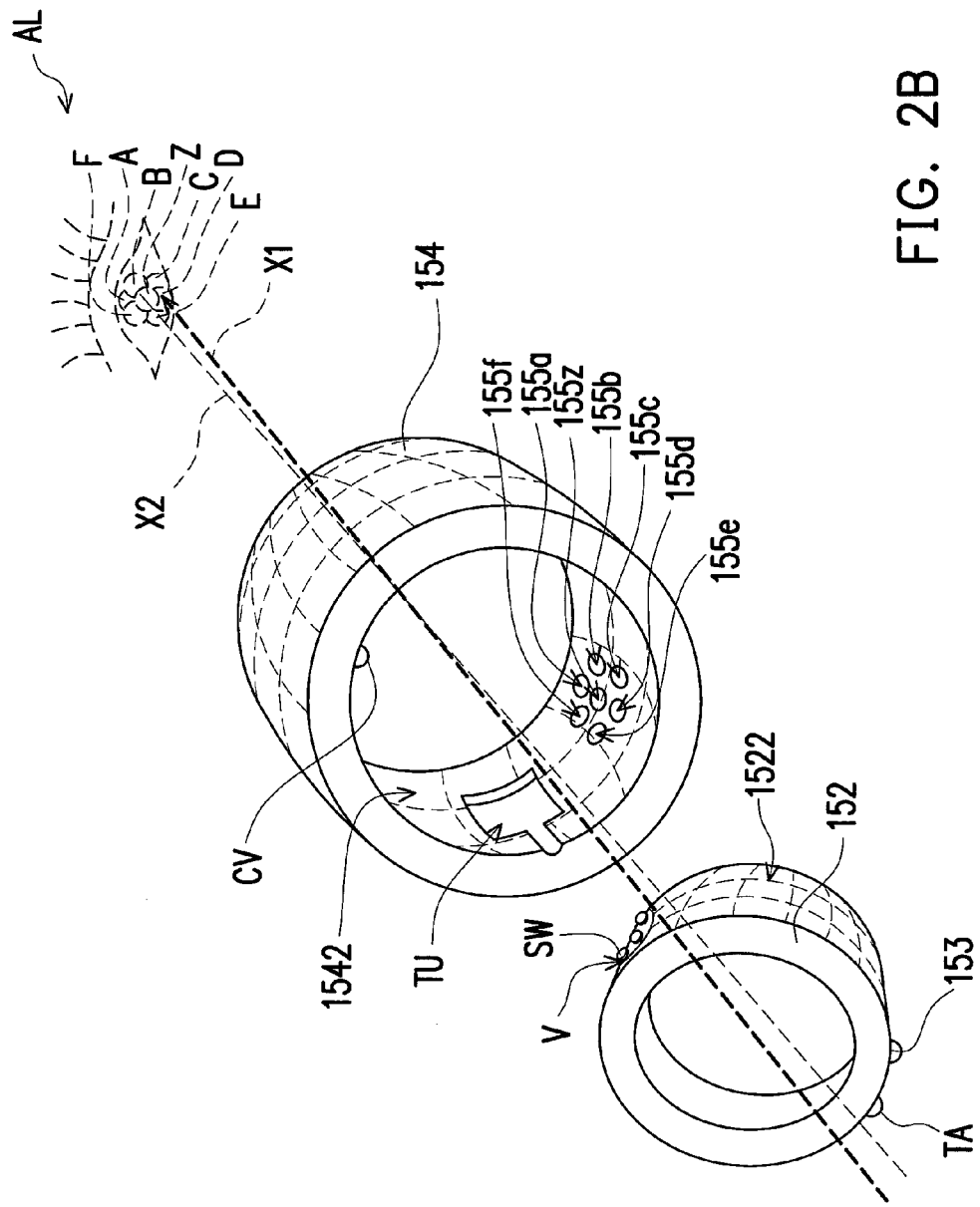

Particularly, in the present embodiment, the front cover 130 is rotatably connected to the lens 120 through a universal joint 150. FIG. 2A and FIG. 2B are schematic partial exploded views illustrating the front cover and the lens depicted in FIG. 1A at two different viewing angles. Please refer to FIG. 2A and FIG. 2B. In the present embodiment, the universal joint 150 has a first element 152 and a second element 154. The first element 152 is connected to the lens 120, and the second element 154 is connected to the front cover 130. In the present embodiment, the first element 152 may be located at one end of the lens 120 close to the front cover 130, and the second element 154 may be located at one end of the front cover 130 close to the lens 120. However, in another embodiment, the first element 152 may be connected to the front cover 130, and the second element 154 may be connected to the lens 120. For instance, the second element 154 may be located at one end of the lens 120 close to the front cover 130, and the first element 152 may be located at one end of the front cover 130 close to the lens 120. In addition, according to the present embodiment, the first element 152 is surrounded by the second element 154. However; according to another embodiment, the second element 154 may be surrounded by the first element 152, which should not be construed as a limitation to the invention. A first positioning portion 153 of the first element 152 is on one side of the first element 152 close to the second element 154, and second positioning portions 155 of the second element 154 are on one side of the second element 154 close to the first element 152. In the present embodiment, an outer surface 1522 of the first element 152 and an inner surface 1542 of the second element 154 are curved surfaces, e.g., two conformal curved surfaces. Therefore, when the first element 152 slides with respect to the second element 154, the first element 152 rotates with respect to the second element 154 as well, and the first positioning portion 153 is selectively wedged on one of the second positioning portions 155. Through said mechanism, the lens 120 connected to the first element 152 may be rotated and aligned to the eyeball at different angles. In the present embodiment, the inner surface 1542, for instance, is a concave surface; the outer surface 1522, for instance, is a convex surface. The outer surface 1522 described herein has a concave groove TU, and the inner surface 1542 has a protrusion TA corresponding to the concave groove TU. When the first element 152 and the second element 154 are assembled to each other, the protrusion TA may be aligned to the concave groove TU, so as to combine the first and second elements 152 and 154. After the protrusion TA enters the concave groove TU, the protrusion TA may be moved in the concave groove TU, such that the first element 152 may be rotated with respect to the second element 154 for performing said functions. In addition, the first element 152 and the second element 154 are not apt to be separated from each other.

To be specific, with reference to FIG. 2A, when the first positioning portion 153 on the first element 152 is wedged on the second positioning portion 155a, the first optical axis X1 of the lens 120 is inclined with respect to the second optical axis X2 of the eyeball in an upward direction, as shown in FIG. 1B, and the imaging unit 110 may capture images at a upper region A of the fundus OP along the first optical axis X1. With reference to FIG. 2B, when the first positioning portion 153 on the first element 152 is wedged on the second positioning portion 155d, the first optical axis X1 of the lens 120 is inclined with respect to the second optical axis X2 of the eyeball in a downward direction, as shown in FIG. 1C, and the imaging unit 110 may capture images at a lower region D of the fundus OP along the first optical axis X1. In detail, when the first element 152 is wedged on one of the second positioning portions 155a, 155b, 155c, 155d, 155e, 155f, and 155z, the first optical axis X1 of the lens 120 may correspondingly be aligned with different parts of the eyeball, i.e., regions A, B, C, D, E, F, and Z of the fundus OP in the present embodiment. Thereby, the imaging unit 110 is able to capture images of different parts of the eyeball, which is conducive to clinical diagnosis of ophthalmic diseases. According to the present embodiment, the first positioning portion 153 is a protrusion, and each of the second positioning portions 155 is a recession, for instance. However, in another embodiment of the invention, the first positioning portion 153 is a recession, and each of the second positioning portions 155 is a protrusion, for instance. Besides, whether the first and second positioning portions 153 and 155 are recessions or protrusions, the shape of the first and second positioning portions 153 and 155, the number thereof, the arrangement thereof, and the locations thereof may be changed according to actual application requirements, and the invention is not limited thereto.

As shown in FIG. 1A, in the present embodiment, the imaging unit 110 includes an image sensor 112 and a control unit 114. The image sensor 112 is located on a transmission path of light from the lens 120 to capture an image generated by the light which comes from the lens 120. The control unit 114 is electrically connected to the image sensor 112, and the control unit 114 combines a plurality of images sensed by the image sensor 112 and located at a plurality of different angles. In the present embodiment, the control unit 114 is a microcontroller unit (MCU), for instance. When the images at different angles respectively correspond to the first positioning portion 153 being wedged on the different second positioning portions 155, the images captured by the image sensor 112 refer to images of the regions A, B, C, D, E, F, and Z of the fundus OP. Through the combination of the images of different regions, the information required for clinical diagnosis of ophthalmic diseases may be substantially obtained.

Figure 3B:
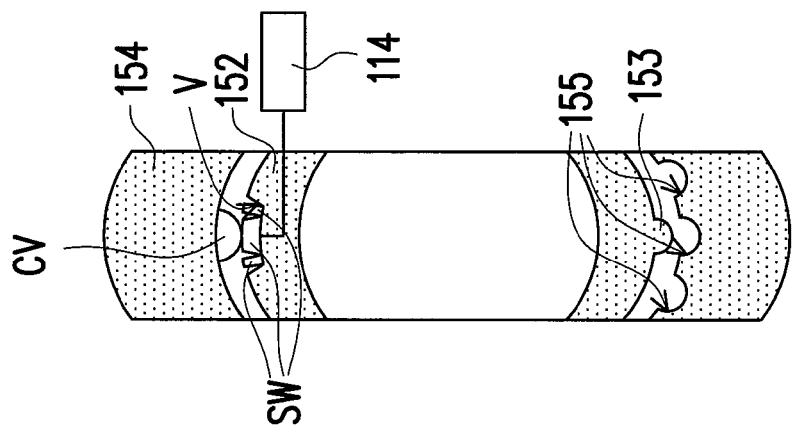
FIG. 3B is a cross-sectional view illustrating the combinative mechanism of the front cover and the lens depicted in FIG. 1A.
Figure 3A:
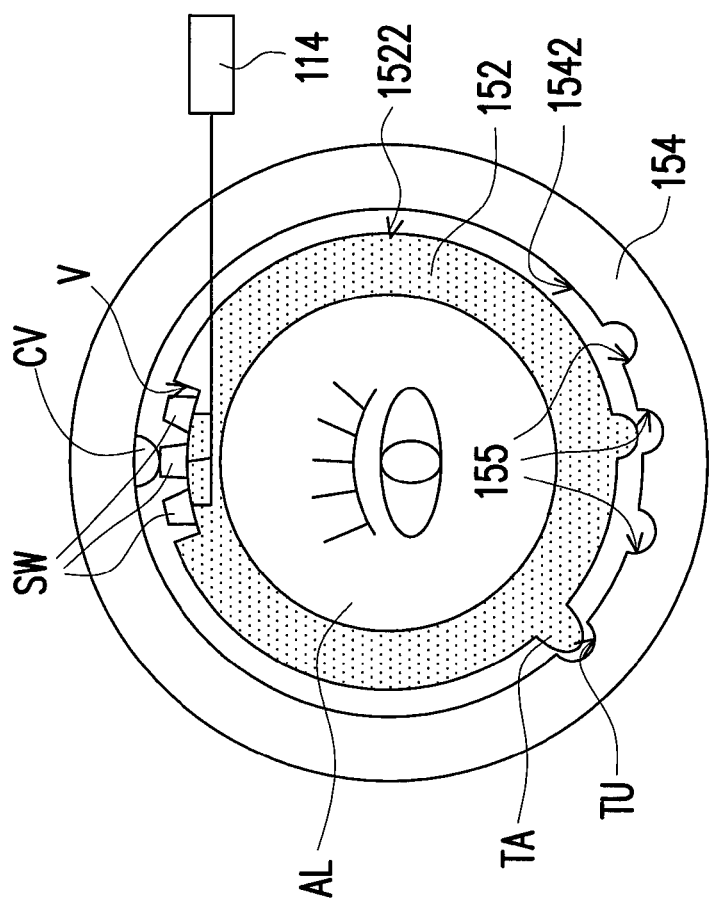
FIG. 3A is a cross-sectional view illustrating the combinative mechanism of the front cover and the lens depicted in FIG. 1A.

FIG. 3A and FIG. 3B are schematic partial cross-sectional views illustrating the front cover and the lens depicted in FIG. 1A at two different viewing angles. With reference to FIG. 1A, FIG. 3A, and FIG. 3B, particularly, the imaging apparatus 110 described in the present embodiment may further include a plurality of switch elements SW electrically connected to the control unit 114. When the first positioning portion 153 is jointed to the different second positioning portions 155, the different switch elements SW are respectively triggered. FIG. 3A and FIG. 3B are schematic partial cross-sectional views illustrating the front cover and the lens depicted in FIG. 1A at two different viewing angles. In the present embodiment, the switch elements SW may be located between the lens 120 and the front cover 130. To be specific, the switch elements SW may be located in cavities V on the outer surface 1522 of the first element 152 and may be electrically connected to the control unit 114, respectively. The switch elements SW described herein are buttons, for instance. However, in another embodiment, the switch elements SW may be contact switches. A conductive loop electrically connected to the control unit 114 may be located on the first positioning portion 153 and has a loop gap which leads to open circuit. When one of the second positioning portions 155 is jointed to the first positioning portion 153, the conductive contact on the second positioning portion 155 is in contact with the loop gap, so as to close the loop (i.e. turn on the loop). In another embodiment, nevertheless, the switch elements SW may refer to mechanical switches and may be positioned at different locations based on actual demands, which should not be construed as a limitation to the invention. When the first positioning portion 153 described herein is jointed to one of the second positioning portions 155, one of the switch elements SW located in the cavities V on the outer surface 1522 of the first element 152 may be in contact with a protrusion CV protruding from the inner surface 1542 of the second element 154 and may then be pressed, so as to generate a signal which is transmitted to the control unit 114. Here, when the first positioning portion 153 is selectively jointed to one of the second positioning portions 155, the switch element SW corresponding to the second positioning portion 155 is pressed down by the protrusion CV, so as to generate the signal. Through the signals, the control unit 114 is able to determine that which switch element SW is being pressed down by the protrusion CV, i.e., the control unit 114 may determine that which second positioning portion 155 is being locked to the first positioning portion 153. Thereby, the control unit 114 may determine the part of the eyeball to which the first optical axis X1 of the lens 120 is directed. Note that the types and the locations of the switch elements SW in the present embodiment are merely exemplary and should not be construed as limitations to the invention.

Figure 4:
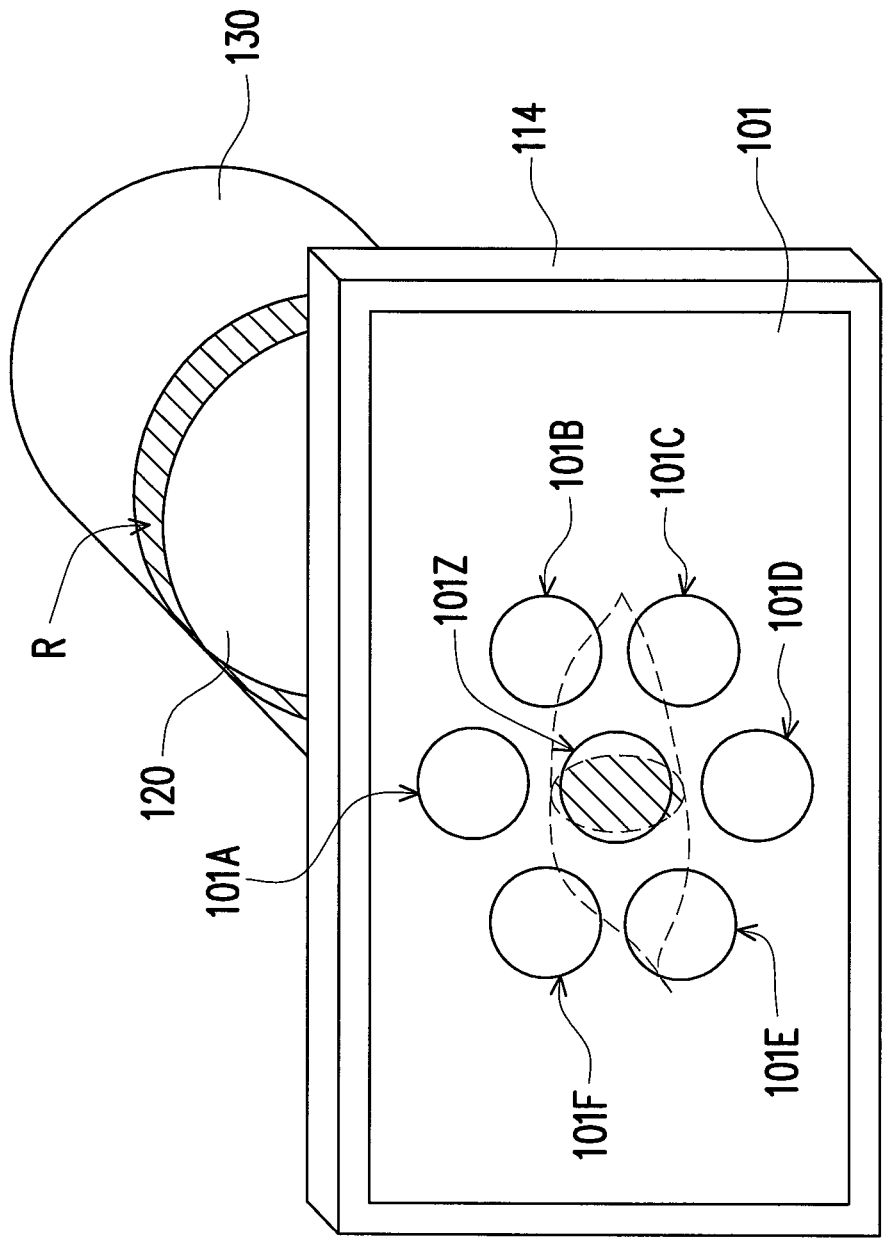
FIG. 4 is a side view illustrating the imaging apparatus depicted in FIG. 1A, FIG. 1B, and FIG. 1C.

According to the present embodiment, the imaging apparatus 100 may further include a user's interface 101 electrically connected to the control unit 114. When one of the switch elements SW is triggered, the user's interface 101 informs a user that the imaging apparatus 100 is located at an image capturing angle corresponding to the triggered switch element SW. FIG. 4 is a side view illustrating the imaging apparatus depicted in FIG. 1A, FIG. 1B, and FIG. 1C. With reference to FIG. 2A, FIG. 2B, and FIG. 4, the user's interface 101 described in the present embodiment may be a liquid crystal display (LCD), an organic light emitting diode (OLED) display, any other appropriate display, or a software interface on a display for instructing a user. As shown in FIG. 4, the user's interface 101 may have instruction regions 101A, 101B, 101C, 101D, 101E, 101F, and 101Z. When the first positioning portion 153 of the first element 152 is wedged on the second positioning portion 155a, the switch element SW located in the cavity V on the outer surface 1522 of the first element 152 is triggered and capable of transmitting a signal to the control unit 114. The control unit 114 is able to determine that the first positioning portion 153 is being wedged on the second positioning portion 155a; namely, the first optical axis X1 of the lens 120 is aligned to the region A of the fundus OP. The control unit 114 is also able to transmit this message to the user's interface 101 and instruct the instruction region 101A on the user's interface to flash, for instance, so as to assist the user in sequentially shooting images of the object AL (e.g., the eye) at various angles. The instruction regions 101A, 101B, 101C, 101D, 101E, 101F, and 101Z of the user's interface 101 not only may correspondingly reflect the locations where the first positioning portion 153 is jointed to the second positioning portions 155 but also may instruct the user to change angles at which the images of the object AL are to be taken. For instance, after the user shoots the images of the region A of the fundus OP, the control unit 114 may instruct the instruction region 101D in the user's interface 101 to flash, so as to guide the user to rotate the lens 120. Thereby, the first positioning portion 153 is jointed to the second positioning portion 155d, i.e., the lens 120 is aligned to the region D of the fundus OP. At this time, the control unit 114 may instruct the instruction region 101D to shine continuously, such that the user is aware that the lens 120 is completely aligned to the region D and images of the region D are ready to be taken. Thereby, repetitive image shooting or omission of image shooing may be prevented, and the images of the fundus may be well combined subsequently. Here, the aforesaid user's interface 101 as well as the number, the shape, and the instruction symbols of the instruction regions are merely exemplary; in another embodiment, the user's interface may be indicative lamps which may achieve the effects similar to those accomplished by the user's interface 101 described herein. The invention is not limited thereto.

The imaging apparatus 100 may be applied not only for observing complete fundus images but also for performing fast and easy fundus examination. For instance, when the first positioning portion 153 of the first element 152 is wedged on the second positioning portion 155a, the first optical axis X1 of the lens 120 is parallel to the second optical axis X2 of the eyeball. That is, at this time, the imaging apparatus 100 is able to capture the images of the region Z at the center of the fundus OP. The instruction region Z of the user's interface 101 may flash at this time, and the control unit 114 may hide the instruction regions A to F or stop flashing the instruction regions A to F, so as to inform the user of entering a mode of simple examination. In case that paramedics intend to observe the images of the fundus OP of a patient in a fast and easy manner, the paramedics may employ the imaging apparatus 100 to directly observe blood vessels and photosensitive cells at the center of the fundus OP. Given that the paramedics intend to further observe the complete images of the fundus OP of the patient, the paramedics may shoot images of the fundus OP at various angles. Thereby, clinical diagnosis of ophthalmic diseases may be flexible and efficient, and quality of medical treatment may be improved as well.

To sum up, in the imaging apparatus provided in an embodiment of the invention, the lens may be rotated with respect to the front cover, and thus the imaging apparatus is capable of shooting images of a to-be-detected object at various angles. Moreover, through the user's interface, the user is able to learn the direction in which the lens is employed to shoot the images, and thus the user may sequentially shoot images of each part of the object in various directions. Thereby, the user is not only able to rapidly shoot the images of the object which may be subsequently combined but also capable of preventing repetitive image shooting or omission of image shooting. Besides, the use of the imaging apparatus is rather simple and convenient. What is more, the imaging apparatus described in an embodiment may perform both the simple examination and the complete examination, and the operational flexibility of the imaging apparatus results in the improvement of efficiency and quality of medical treatment. From another perspective, the imaging apparatus described in an embodiment is not bulky and has the simple structure. Accordingly, the imaging apparatus may be mass-produced and cost-effective, which is also conducive to the improvement of efficiency and quality of medical treatment.

It will be apparent to those skilled in the art that various modifications and variations can be made to the structure of the disclosed embodiments without departing from the scope or spirit of the invention. In view of the foregoing, it is intended that the invention cover modifications and variations of this invention provided they fall within the scope of the following claims and their equivalents.

What is claimed is:

1. An imaging apparatus configured to capture an image of an object to be detected, the imaging apparatus comprising:
    an imaging unit, comprising a control unit;
    a lens located on the imaging unit and having a first optical axis;
    a front cover, wherein the lens is rotatably connected to the front cover, relative locations of the front cover and the object are fixed by leaning the front cover against a structure surrounding the object, and the lens is rotated with respect to the front cover, such that the first optical axis is rotated with respect to the object, and wherein no other lens is fixed on the front cover and rotates with the front cover, the front cover is rotatably connected to the lens through a universal joint, and the universal joint is a first cylinder rotatably mounted within a second cylinder, and wherein one of the first cylinder and the second cylinder is connected to the lens, the other of the first cylinder and the second cylinder is connected to the front cover, the first cylinder has a first positioning portion, the second cylinder has a plurality of second positioning portions, when the lens is rotated with respect to the front cover, the first positioning portion is selectively jointed to one of the second positioning portions, wherein-when the first positioning portion is jointed to the-second positioning portions located on different locations, the lens is respectively in different orientations with respect to the front cover;
    a plurality of switch elements electrically connected to the control unit, wherein when the first positioning portion is jointed to the different second positioning portions, the switch elements are respectively triggered; and
    a user's interface electrically connected to the control unit, wherein when one of the switch elements is triggered, the user's interface informs a user that the imaging apparatus is located at an image capturing angle corresponding to the one of the switch elements, and wherein the user's interface is a display unit, when the switch elements are respectively triggered, the display unit respectively shows different patterns, and locations of the patterns on the display unit respectively correspond to the orientations of the lens with respect to the front cover.

2. The imaging apparatus as recited in claim 1, wherein the object is an eyeball having a second optical axis, and the first optical axis is rotated with respect to the second optical axis when the lens is rotated with respect to the front cover.

3. The imaging apparatus as recited in claim 1, wherein the imaging unit comprises:
    an image sensor located on a transmission path of light from the lens to capture an image generated by the light coming from the lens
    wherein the control unit is electrically connected to the image sensor, the control unit combines a plurality of images sensed by the image sensor and located at a plurality of different angles, and wherein the images at the different angles are captured by the image sensor when the first positioning portion is jointed to the different second positioning portions.

4. The imaging apparatus as recited in claim 1, wherein the switch elements are located between the lens and the front cover.

5. The imaging apparatus as recited in claim 1, wherein the control unit selectively instructs the display unit to flash one of the patterns, so as to remind the user of rotating the lens with respect to the front cover to an orientation corresponding to the flashed one of the patterns, and when the lens is rotated with respect to the front cover to the orientation corresponding to the flashed one of the patterns, the control unit instructs the display unit to continuously show the one of the patterns.

6. The imaging apparatus as recited in claim 1, wherein the front cover comprises a lens ring close to a junction of the front cover and the lens, and a user holds the lens ring to rotate the front cover with respect to the lens.

7. The imaging apparatus as recited in claim 1, wherein the object is an eyeball, and the front cover leans against tissues surrounding the eyeball.

* * * * *